(12) United States Patent
Loxley et al.

(10) Patent No.: US 11,246,831 B2
(45) Date of Patent: Feb. 15, 2022

(54) PARTICLE FORMULATIONS AND USES THEREOF

(75) Inventors: Andrew Loxley, Philadelphia, PA (US); Mark Mitchnick, East Hampton, NY (US); David Fairhurst, Congers, NY (US); Christy Ann Eatmon, Bethlehem, PA (US)

(73) Assignee: PARTICLE SCIENCES, INC., Bethlehem, PA (US)

( * ) Notice: Subject to any disclaimer, the term of this patent is extended or adjusted under 35 U.S.C. 154(b) by 17 days.

(21) Appl. No.: 12/593,029

(22) PCT Filed: Mar. 31, 2008

(86) PCT No.: PCT/US2008/058835
§ 371 (c)(1),
(2), (4) Date: Nov. 18, 2009

(87) PCT Pub. No.: WO2008/121926
PCT Pub. Date: Oct. 9, 2008

(65) Prior Publication Data
US 2010/0062071 A1 Mar. 11, 2010

Related U.S. Application Data

(60) Provisional application No. 60/956,702, filed on Aug. 19, 2007, provisional application No. 60/909,272, filed on Mar. 30, 2007.

(51) Int. Cl.
| | | |
|---|---|---|
| A61K 9/10 | (2006.01) |
| A61K 9/51 | (2006.01) |
| A61K 39/39 | (2006.01) |
| A61K 39/00 | (2006.01) |

(52) U.S. Cl.
CPC .............. *A61K 9/10* (2013.01); *A61K 9/5123* (2013.01); *A61K 39/39* (2013.01); *A61K 2039/55555* (2013.01)

(58) Field of Classification Search
None
See application file for complete search history.

(56) References Cited

U.S. PATENT DOCUMENTS

| | | | | |
|---|---|---|---|---|
| 4,880,634 A | * | 11/1989 | Speiser | A61K 9/5123 |
| | | | | 424/450 |
| 5,393,461 A | | 2/1995 | Fillipova | 252/314 |
| 5,716,637 A | | 2/1998 | Anselem et al. | 424/450 |
| 5,889,088 A | * | 3/1999 | Kisuno et al. | 523/205 |
| 5,965,144 A | | 10/1999 | Podolski et al. | 424/278.1 |
| 2006/0029661 A1 | * | 2/2006 | Radhakrishnan et al. | 424/456 |

FOREIGN PATENT DOCUMENTS

| | | |
|---|---|---|
| EP | 08744731 | 10/2012 |
| WO | WO 97/47320 | 12/1997 |
| WO | WO 02/076441 A1 | 10/2002 |
| WO | 2004/069227 A1 | 8/2004 |
| WO | WO 2005/041933 A1 | 5/2005 |

OTHER PUBLICATIONS

"The Effects of Temperature and Time on Beeswax and Honey," retrieved from <http://www.honeyshop.co.uk/effect.html>.*
"Sorting Out Surfactants," Stavroudis, C., WAAC Newsletter 31(1): 19-21 (2009).*
Hepatitis B Vaccine, as accessed at https://en.wikipedia.org-/wiki/Hepatitis_B_vaccine, on Feb. 1, 2017.*
CTAB, accessed from the Internet at <https://www.sigmaaldrich.com/catalog/search?term-=CTAB&interface=AII&N=0&mode=match%20partialmax&lang=en&region=US&focus=product> on Aug. 14, 2019. (Year: 2019).*
Bodmeier et al. "Process and Formulation Variables in the Preparation of Wax Microparticles by a Melt Dispersion Technique. I Oil-in-Water Technique for Water-Insoluble Drugs" Journal of Microencapsulation 1992 vol. 9 (1): 89-98.
Ma et al. "Development of Idarubicin and Doxorubicin Solid Lipid Nanoparticles to Overcome Pgp-Mediated Multiple Drug Resistance in Leukemia" Journal of Biomedical Nanotechnology 2009 vol. 5 (2): 151-161.
Myc et al. "Development of Immune Response That Protects Mice from Viral Pneumonitis After a Single Intranasal Immunization with Influenza a Virus and Nanoemulsion" Vaccine 2003 vol. 21: 3801-3814.
Panda et al. "Studies of Immune Response by Antigen Loaded Biodegradable Polymer Particles" http://www.nii.res.in/res2002/resim027.html.
Rudolph et al. "Application of Novel Solid Lipid Nanoparticle (SNL)-Gene Vector Formulations Based on a Dimeric HIV-1 TAT-Peptide in Vitro and in Vivo" Pharmaceutical Research 2004 vol. 21 (9): 1662-1669.
Cui et al. "Physical Characterization and Macrophage Cell Uptake of Mannan-Coated Nanoparticles" Drug Development and Industrial Pharmacy 2003 29(6):689-700.
Cui et al. "Lecithin-based Cationic Nanoparticles as a Potential DNA Delivery System" International Journal of Pharmaceutics 2006 313:206-213.

* cited by examiner

*Primary Examiner* — David J Blanchard
*Assistant Examiner* — Daniel F Coughlin
(74) *Attorney, Agent, or Firm* — Licata & Tyrrell P.C.

(57) ABSTRACT

Aqueous dispersions of chemically and physically stable particles for use in delivery of active pharmaceutical ingredients and processes for their production and use to enhance a biological response to an active pharmaceutical ingredient and prophylactically or therapeutically treat a subject are provided. Vaccines, wherein the active pharmaceutical ingredient is a solution of subunit vaccine antigen mixed with a colloidal dispersion of electrically charged particles and use of such vaccines in immunization are also provided.

6 Claims, 3 Drawing Sheets

Apparent attachment efficiency of gp 140 to nanoparticles (Bradford assay)

| Particle type | Attachment efficiency |
|---|---|
| YC-brij-chitosan | 76.7 |
| YC-SDS | 85.0 |
| YC-1% NaMA | 99.6 |

FIG. 2

PARTICLE FORMULATIONS AND USES THEREOF

This patent application is a U.S. National Stage Application of PCT Patent Application No. PCT/US2008/058835, filed Mar. 31, 2008, which claims the benefit of priority from U.S. Provisional Patent Application Ser. No. 60/956,702, filed Aug. 19, 2007 and U.S. Provisional Patent Application Ser. No. 60/909,272, filed Mar. 30, 2007, teachings of each of which are herein incorporated by reference in their entirety.

FIELD OF THE INVENTION

The present invention relates to chemically and physically stable particle formulations for use in delivery of active pharmaceutical ingredients and processes for their production. Such particle formulations are particularly useful as vaccines wherein a colloidal dispersion of electrically charged particles is mixed with a solution of subunit vaccine antigens. The present invention also relates to methods of enhancing a biological response to an active pharmaceutical ingredient via formulation of the active pharmaceutical ingredient with the chemically and physically stable particles and to methods for preparation and use of these formulations of active pharmaceutical ingredient with the chemically and physically stable particles prophylactically and/or therapeutically.

BACKGROUND OF THE INVENTION

Various particle formulations for use as vaccines are known.

For example, Freund's adjuvant is a mineral oil droplet emulsion used routinely in experimental vaccines to stimulate the immune system. Freund's adjuvant is toxic in humans and is not used in commercial human vaccines.

The recently released quadrivalent HPV-6/11/16/18 virus-like-particle vaccine GARDASIL® (Merck & Co.) comprises relatively large particles of amorphous aluminum hydroxyphosphate sulfate adjuvant.

An antimicrobial nanoemulsion composed of soybean oil, emulsifying agents, and ethanol has also been described. The emulsion has 200 nM particles that inactivate enveloped viruses by fusing with the virus and disrupting its membrane. When this material was mixed with influenza virus and placed into the nares of animals, it produced rapid and intense immune responses that protected animals from subsequent virus challenge. This immunity was achieved with only a single application of virus and nanoemulsion and involved both mucosal and cytotoxic components. (Myc et al. Vaccine 21(25-26); 2003, 3801-3814).

Charged emulsifying-wax nanometer-sized safe lipid particles for use in delivery of chemotherapeutic agents such as paclitaxel to target breast cancer cells have also been described by Mumper (mc with the extension uky.edu/pharmacy/new_archive.asp?id=92 of the world wide web).

Entrapping tetanus toxoid antigen in degradable polymer particles, in particular PLA particles, via solvent evaporation to enhance the immune response to this antigen has also been described (Panda et al. nii with the extension .res.in/res2002/resim027.html of the world wide web).

Adsorbing tetanus toxoid antigen to the surface of charged polyester particles has also been described.

In addition, Rudolph et el. (*Pharmaceutical Research* 2004 21 (9):1662-1669) describe an aqueous dispersion of solid lipid nanoparticles (SLN) of cetylpalmitate and the cationic lipid N,N-di-(β-stearoylethyl)-N,N-dimethyl-ammonium chloride or 1,2-dioleyl-sn-glycero-3-trimethylammoniumpropane (DOTAP) to which DNA was adsorbed to the surface for lung delivery. They showed expression of the DNA-encoded protein after delivery from a nebulized aerosol to the lungs of mice.

SUMMARY OF THE INVENTION

An aspect of the present invention relates to an aqueous dispersion of chemically and physically stable particles having an average diameter of less than 100 μm and comprising a hydrophobic organic material stable to aqueous hydrolysis which interacts with a co-dissolved or co-dispersed active pharmaceutical ingredient.

Another aspect of the present invention relates to a composition comprising a water-soluble or water-dispersible active pharmaceutical ingredient and an aqueous dispersion of chemically and physically stable particles having an average diameter of less than 100 μm and comprising a hydrophobic organic material stable to aqueous hydrolysis which interacts with the water-soluble or water-dispersible active pharmaceutical ingredient. In one embodiment, the composition is a vaccine formulation comprising a mixture of a subunit vaccine antigen and a colloidal dispersion of electrically charged particles.

Another aspect of the present invention relates to a process for formulating compositions for delivery of an active pharmaceutical ingredient which comprises mixing a solution or dispersion of water-soluble or water-dispersible active pharmaceutical ingredient with an aqueous dispersion of chemically and physically stable particles having an average diameter of less than 100 μm, said particles comprising a hydrophobic organic material stable to aqueous hydrolysis, so that said particles interact with the co-dissolved or co-dispersed active pharmaceutical ingredient. In one embodiment, the process is used to produce a vaccine formulation by mixing a solution of a subunit vaccine antigen with a pre-formed colloidal dispersion of electrically charged particles.

Another aspect of the present invention relates to a method for enhancing a biological response to an active pharmaceutical ingredient which comprises administering the active pharmaceutical ingredient as a composition comprising a water-soluble or water-dispersible active pharmaceutical ingredient and an aqueous dispersion of chemically and physically stable particles having an average diameter of less than 100 μm and comprising a hydrophobic organic material stable to aqueous hydrolysis which interacts with the water-soluble or water-dispersible active pharmaceutical ingredient.

Yet another aspect of the present invention relates to methods for use of these formulations of active pharmaceutical ingredient with the chemically and physically stable particles prophylactically and/or therapeutically. In one embodiment, a method is provided for immunizing a subject against an antigen that comprises administering to the subject a vaccine formulation comprising a mixture of a subunit vaccine antigen and a colloidal dispersion of electrically charged particles.

BRIEF DESCRIPTION OF THE FIGURES

FIG. 2 is a bar graph showing the ability of exemplary hydrophobic organic material particles, prepared in accordance with the present invention with additional components to decorate the particle of the surface and/or make the surface charged, to interact with the protein gp140. In this experiment, particles comprised yellow carnauba wax (YC) and were prepared with the additional components Brij700 and chitosan, sodium dodecyl sulfate (SDS) or sodium myristate (NaMa). As shown, both cationic (YC-Brij-chitosan) and anionic (YC-SDS and YC-1% NaMa) particles efficiently attached the protein.

DETAILED DESCRIPTION OF THE INVENTION

Figure 1A:
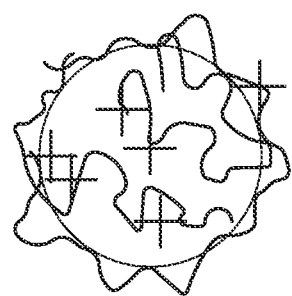
FIGS. 1A and 1B are models of cationic (FIG. 1A) and anionic (FIG. 1B) particles used in the aqueous dispersion of the present invention.

The present invention relates to an aqueous dispersion of chemically and physically stable particles useful in preparations of compositions comprising active pharmaceutical ingredients.

Particles of the aqueous dispersion of the present invention interact with a co-dissolved or co-dispersed active pharmaceutical ingredient.

By interaction or interacts, as used herein, it is meant that the active pharmaceutical ingredient attaches, adheres to or binds to the particle. While not being bound to any theory, it is believed that this interaction may occur through electrostatic or hydrophobic forces.

In one exemplary embodiment, the particles comprise a hydrophobic organic material stable to aqueous hydrolysis. Examples of hydrophobic organic materials useful in the present invention include, but are in no way limited to, organic waxes such as bees wax and carnauba wax, cetyl alcohol, ceteryl alcohol, behenyl alcohol, fatty acids, and fatty acid esters. Preferred for use in the particles is an organic wax with a melting point above 25° C. In some embodiments, the hydrophobic organic material particles may further comprise a pharmaceutically acceptable oil. Examples of pharmaceutically acceptable oils include, but are not limited to, mineral oil, oils of vegetable origin (maize, olive, peanut, soybean etc) and silicone fluids such as Dow Corning DC200. For these embodiments, the particles may comprise 1% to 100% of an organic wax with a melting point above 25° C. and 0 to 99% of a pharmaceutically acceptable oil.

Preferred are electrically charged particles of a hydrophobic organic material.

An additional exemplary embodiment of electrically charged particles useful in the present invention is particles comprised of water-insoluble metal oxides.

Another exemplary embodiment of electrically charged particles useful in the present invention is particles comprised of polymersomes.

Another exemplary embodiment of electrically charged particles useful in the present invention is particles comprised of phospholipid vesicles such as liposomes. Liposomes can be prepared in accordance with any of the well known methods such as described by Epstein et al. (Proc. Natl. Acad. Sci. USA 82: 3688-3692 (1985)), Hwang et al. (Proc. Natl. Acad. Sci. USA 77: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Preferred liposomes are of the small (about 200-800 Angstroms) unilamellar type in which the lipid content is greater than about 10 mol. percent cholesterol, preferably in a range of 10 to 40 mol. percent cholesterol, the selected proportion being adjusted for optimal vaccine therapy. However, as will be understood by those of skill in the art upon reading this disclosure, phospholipid vesicles other than liposomes can also be used.

Another exemplary embodiment of electrically charged particles useful in the present invention are particles comprised of pharmaceutically acceptable oil droplets, preferably with an average size above 400 nm. Examples of pharmaceutically acceptable oils include, but are not limited to, mineral oil, oils of vegetable origin (maize, olive, peanut, soybean etc) and silicone fluids such as Dow Corning DC200.

Yet another exemplary embodiment of electrically charged particles useful in the present invention is particles comprised of surfactant or block copolymer micelles.

In a preferred embodiment, particles used in the aqueous dispersions of the present invention are prepared with an additional component to decorate the particle of the surface and/or make the surface charge. Examples of such components include, but are not limited to chitosan, charged emulsifiers such as sodium dodecyl sulfate and fatty acids or salts thereof. Examples of fatty acids include, but are not limited to, myristic acid and behenic acid.

In one embodiment, dispersions of the electrically charged particles are stabilized via an emulsifier. Addition of the emulsifier enables the formation of particles in the dispersion step and if charged makes the surface charged.

For positively charged or cationic particles (see FIG. 1A) a cationic emulsifier can be used. Examples of components useful in preparation of cationic particles include, but are not limited to, emulsifiers cetyltrimethylammonium bromide and cetyle pyridinium halide and the cationic polymer is chitosan. In one exemplary embodiment, chitosan is added along with the non-ionic emulsifier Brij700 to make the otherwise neutral particles into cationic ones. As will be understood by the skilled artisan upon reading this disclosure, alternative cationic emulsifiers can also be used.

Figure 1B:
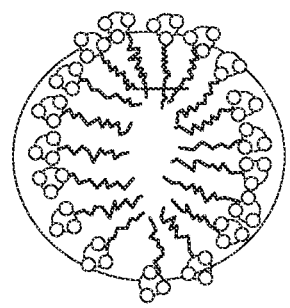

For negatively charged or anionic particles (see FIG. 1B) an anionic emulsifier can be used. Preferred anionic emulsifiers for use in the present invention include, but are not limited to sodium dodecyl sulfate and sodium myristate. As will be understood by the skilled artisan upon reading this disclosure, alternative anionic emulsifiers can also be used.

Alternatively, a non-ionic emulsifier such as Brij700 and a cationic polymer such as chitosan-acetate can be added to the particles to makes them stable and positively charged. Again, as will be understood by the skilled artisan upon reading this disclosure, alternative nonionic emulsifiers and cationic or anionic polymers can be used.

The particles of the dispersions of the present invention have an average diameter of less than 100 μm, more preferably less than 10 μm, more preferably less than 1 μm.

In one embodiment of the present invention, the particles are used in vaccine formulations. In this embodiment, the vaccine formulation comprises a mixture of a subunit vaccine antigen, preferably in solution, and electrically charged particles, preferably in a pre-formed colloidal dispersion. In this embodiment, for vaccine formulations, it is preferred that the particles have a mean particle diameter of less than 20 microns, more preferably less than 10 microns, and most preferably less than 1 micron.

In some embodiments, the particles may further comprise a small-molecule microbicide such as TMC120 to provide a vaccine-microbicide combination.

Alternatively, or in addition, in some embodiments the particles further comprise moieties that are ligands for surface receptors on the cells where the particles are to be delivered, and target the particles to those cells. For example, a polysaccharide recognized by cell surface receptors such as mannose receptor can be placed at the particle surface, thereby improving particle internalization by cells carrying those receptors.

In a preferred embodiment, particles for use in the aqueous dispersion of the present invention are prepared via a process essentially free from organic solvents.

In one embodiment, the process comprises heating the solid lipid or wax above its melt temperature to form a molten lipid or wax. Particles are formed by dispersing the molten material into an aqueous emulsifier solution using high shear such as that provided by an ultrasonic horn, or a high-pressure homogenizer, until the particle size of the dispersed phase is submicron. The thus-formed hot oil-in-water nanoemulsion is then cooled to room temperature to harden the lipid or wax nanodroplets, forming an aqueous dispersion of lipid or wax nanoparticles, stabilized by the emulsifier.

The aqueous dispersions are useful in formulating compositions comprising the aqueous dispersion and a water-soluble or water-dispersible active pharmaceutical ingredient. As shown in FIG. 2, both cationic particles and anionic particles of the present invention are efficient at interacting with an active pharmaceutical ingredient.

Active pharmaceutical ingredients which can interact with particles in the aqueous dispersion to formulate these compositions include, but are in no way limited to, drugs, including vaccines, nutritional agents, cosmeceuticals and diagnostic agents. Examples of active pharmaceutical ingredients for use in the present invention include, but are not limited to analgesics, anti-anginal agents, anti-asthmatics, anti-arrhythmic agents, anti-angiogenic agents, antibacterial agents, anti-benign prostate hypertrophy agents, anti-cystic fibrosis agents, anti-coagulants, anti-depressants, anti-diabetic agents, anti-epileptic agents, anti-fungal agents, anti-gout agents, anti-hypertensive agents, anti-inflammatory agents, anti-malarial agents, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anxiolytics, beta-blockers, cardiac inotropic agents, cognition enhancers, corticosteroids, COX-2 inhibitors, diuretics, erectile dysfunction improvement agents, essential fatty acids, gastrointestinal agents, histamine receptor antagonists, hormones, immunosuppressants, keratolyptics, leukotriene antagonists, lipid regulating agents, macrolides, muscle relaxants, non-essential fatty acids, nutritional agents, nutritional oils, protease inhibitors and stimulants.

Aqueous dispersion of particles of the present invention are particularly useful in vaccine formulations wherein the active pharmaceutical ingredient is a protein, preferably a subunit vaccine antigen such as, but not limited to, tetanus toxoid or gp140, or a nucleic acid such as, but not limited to, DNA, RNA, ShRNA, ShRNA, or an antisense oligonucleotide.

Vaccine formulations of the present invention may further comprise an anionic adjuvant such as, but not limited to, poly(IC) or CpGB. In some embodiments, the adjuvant is adsorbed to the particle surface.

Such compositions can be formulated by various processes. In one embodiment, a composition is prepared by mixing a solution or dispersion of water-soluble or water-dispersible active pharmaceutical ingredient with an aqueous dispersion of the present invention. The chemically and physically stable particles in the aqueous dispersion which comprise a hydrophobic organic material stable to aqueous hydrolysis interact with the co-dissolved or co-dispersed active pharmaceutical ingredient to form the compositions.

Figure 3:
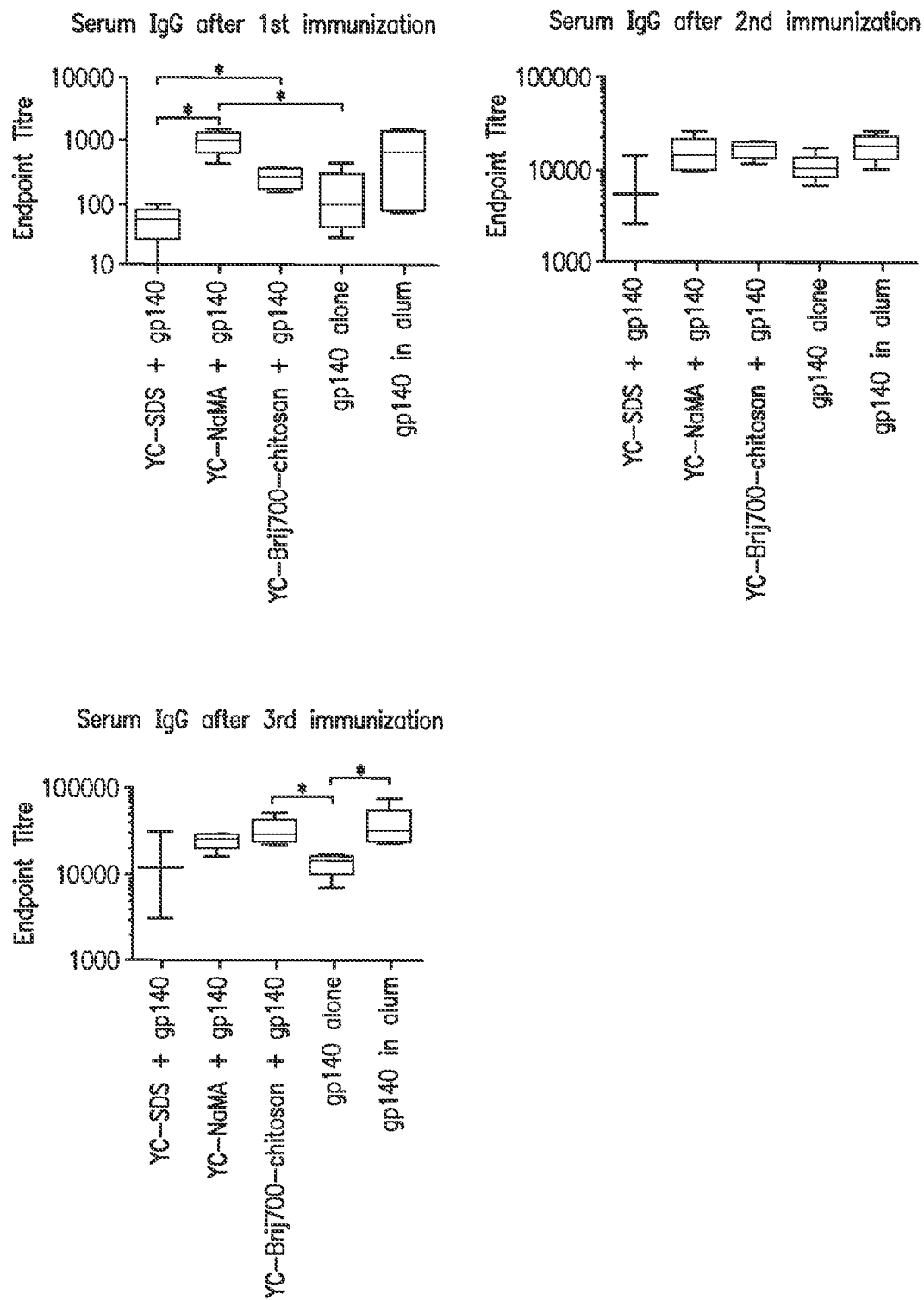
FIG. 3 provides graphs of the results from experiments in mice immunized with compositions of the present invention. Mice (n=4/group) were immunized with either: YC-SDS particles with gp140 (10 μg); YC-NaMA particles with gp140 (10 μg); YC-Brij700-chitosan with gp140 (10 μg); gp140 alone (10 μg); or gp140 (10 μg) +adjuvant (alum). Each animal received three doses, prime, boost and boost. Groups 1-4 were administered the same antigen delivery each time. In Group 5, the first dose was antigen with adjuvant while the second and third doses were antigen alone. The compositions were administered subcutaneously at an injection volume (antigen+formulation in saline) of 100 μl/dose. Blood samples were taken at each immunization and 4 weeks post final dose. Serum IgG levels were determined after the first, second and third immunizations.

Compositions produced in accordance with the present invention comprising an active pharmaceutical ingredient which interacts with the chemically and physically stable particles in the aqueous dispersion exhibit an enhanced biological response to the active pharmaceutical ingredient as compared to active pharmaceutical ingredient administered alone. As shown in FIG. 3, mice immunized with a composition comprising an aqueous dispersion of anionic particles and the active pharmaceutical ingredient gp140 (YC-NaMA particles with gp140 (10 μg)) and mice immunized with a composition comprising an aqueous dispersion of cationic particles and the active pharmaceutical ingredient gp140 (YC-Brij700-chitosan with gp140 (10 μg)) exhibited an antibody response greater than that in mice administered gp140 alone and similar to mice administered gp140 with the known adjuvant alum. Accordingly, the compositions of the present invention can be administered to enhance the biological response to an active pharmaceutical ingredient.

Compositions of the present invention are thus useful prophylactically and therapeutically in treatment of a subject suffering from a disorder or disease treatable with the active pharmaceutical ingredient of the composition.

In one embodiment, wherein the active pharmaceutical ingredient in a subunit vaccine antigen and the composition is a vaccine formulation, the composition can be administered to a subject to immunize the subject against an antigen.

By "subject" as used herein it is meant an animal, preferably a mammal, more preferably a human.

The following nonlimiting examples are provided to further illustrate the present invention.

Examples

Example 1

Preparation and Characterization of Exemplary Particles

The following exemplary particles for use in the aqueous dispersions of the present invention were prepared via a process essentially free from organic solvents. Surface chemistries and properties of the surface of particles with these chemistries were determined.

Microparticle Formulations

| matrix material | surface nature | surface chemistry | properties |
|---|---|---|---|
| carnuba wax | sulfate | SDS | anionic, hydrophobic, hard |
| | carboxylate | myristic acid | anionic, hydrophobic, hard |
| | PEG | steareth-100 | non-ionic, hydrophobic, hard |
| | N-acetylglucosamine | chitosan | cationic, hydrophobic, hard |
| | quaternary amine | cetyl trimethylammonium bromide | cationic, hydrophobic, hard |
| bees wax | sulfate | SDS | anionic, hydrophobic, soft |
| | carboxylate | myristic acid | anionic, hydrophobic, soft |
| | PEG | steareth-100 | non-ionic, hydrophobic, soft |
| | N-acetylglucosamine | chitosan | cationic, hydrophobic, soft |
| | quaternary amine | cetyl trimethylammonium bromide | cationic, hydrophobic, soft |
| cetyl alcohol | carboxylate | behenic acid | anionic, more hydrophilic, soft |

Example 2

Preparation of Exemplary Vaccine Formulation

Aqueous wax dispersions were prepared by melting a natural wax and emulsifying this liquid wax into a hot aqueous surfactant solution with high shear to form an emulsion with submicron droplets of the molten wax. Cooling the emulsion leads to solidification of the dispersed and stabilized nanodroplets to yield a stable dispersion of wax nanoparticles.

In an effort to develop a mucosally applied HIV-1 vaccine, tetanus toxoid was used as a model subunit vaccine antigen. It was found that upon mixing of tetanus toxoid antigen with an aqueous dispersion of sub-micron sized yellow-carnauba wax particles, the tetanus toxoid antigen protein adsorbed to the particle surface. When this formulation (wax nanoparticles+antigen) was incubated in-vitro with blood cells derived from tetanus-vaccinated donors, statistically significantly higher T-cell proliferation was observed compared to cells incubated with free tetanus toxoid at the same total concentration, and similar to free tetanus toxoid mixed with the vaccine adjuvant poly(I:C). Thus, when antigens are mixed with the wax particles, the immune response to the antigen mixed with the particles is increased. Also no activation of the immune system was observed for the particles alone, making them non-immunogenic.

T-cell proliferation was observed when the yellow carnauba dispersion was prepared with the following emulsifiers:
1. SDS (sodium dodecyl sulfate, forming anionic particles)
2. NaMA (Sodium myristate, forming anionic particles), or
3. Brij700+chitosan (Brij700 is a non-ionic stearethpolyethylene glycol (100), chitosan is a cationic polysaccharide, forming cationic particles)

What is claimed is:

1. A process for formulating a composition comprising an aqueous dispersion of chemically and physically stable particles having an average diameter of less than 100 μm mixed and a water-soluble or water-dispersible active pharmaceutical ingredient, said process comprising forming an aqueous dispersion of chemically and physically stable particles having an average diameter of less than 100 μm using high shear provided by an ultrasonic horn or a high-pressure homogenizer via a process free from organic solvents, said particles consisting of a hydrophobic organic material stable to aqueous hydrolysis, the hydrophobic organic material comprising carnauba wax or beeswax, which material interacts with a co-dissolved or co-dispersed active pharmaceutical ingredient, and one or more surfactants or emulsifiers selected from the group consisting of cetyltrimethylammonium bromide, cetyl pyridinium halide, chitosan, chitosan-acetate, polyetholylated stearyl alcohol, sodium dodecyl sulfate, sodium myristate and fatty acids or salts thereof and mixing said particles with a water-soluble or water-dispersible active pharmaceutical ingredient so that the water-soluble or water-dispersible active pharmaceutical ingredient is adsorbed to a surface of said particles.

2. The method of claim 1 where said particles have an average diameter of less than 10 μm.

3. The method of claim 1 where said particles have an average diameter of less than 1 μm.

4. The method of claim 1 wherein the active pharmaceutical ingredient comprises a protein.

5. The method of claim 1 wherein the active pharmaceutical ingredient comprises an antigen.

6. The method of claim 1 wherein the formulated composition is a vaccine.

* * * * *